US00PP27899P3

(12) United States Plant Patent
Growns

(10) Patent No.: US PP27,899 P3
(45) Date of Patent: Apr. 18, 2017

(54) ***GREVILLEA* PLANT NAMED 'KINGS CELEBRATION'**

(50) Latin Name: ***Grevillea* hybrid**
Varietal Denomination: Kings Celebration

(71) Applicant: Botanic Gardens and Parks Authority, West Perth (AU)

(72) Inventor: Digby Growns, Canning Vale (AU)

(73) Assignee: Botanic Gardens and Parks Authority, West Perth (AU)

( * ) Notice: Subject to any disclaimer, the term of this patent is extended or adjusted under 35 U.S.C. 154(b) by 94 days.

(21) Appl. No.: 14/756,474

(22) Filed: Sep. 8, 2015

(65) Prior Publication Data

US 2016/0345478 P1 Nov. 24, 2016

Related U.S. Application Data

(60) Provisional application No. 62/230,012, filed on May 22, 2015.

(51) Int. Cl.
*A01H 5/02* (2006.01)

(52) U.S. Cl.
USPC ..... Plt./226

(58) Field of Classification Search
USPC ..... Plt./226
See application file for complete search history.

*Primary Examiner* — Anne Grunberg
(74) *Attorney, Agent, or Firm* — Audrey Charles

(57) ABSTRACT

A new and distinct cultivar of *Grevillea* plant named 'Kings Celebration', characterized by its bright red-colored inflorescences, medium green-colored foliage, and moderately vigorous, upright growth habit, is disclosed.

1 Drawing Sheet

Latin name of genus and species of plant claimed: *Grevillea* hybrid.

Variety denomination: 'Kings Celebration'.

BACKGROUND OF THE INVENTION

The present invention relates to a new and distinct cultivar of *Grevillea* plant botanically known as *Grevillea* hybrid and hereinafter referred to by the cultivar name 'Kings Celebration'.

The new cultivar originated in a controlled breeding program in West Perth, Australia during February 2008. The objective of the breeding program was the development of *Grevillea* cultivars that have large inflorescences with attractive colors.

The new *Grevillea* cultivar is the result of cross-pollination. The female (seed) parent of the new cultivar is a *Grevillea fastigiata* proprietary breeding selection not coded, not patented, characterized by its medium red-colored inflorescences, medium green-colored foliage, and moderately vigorous, prostrate growth habit. The male (pollen) parent of the new cultivar is *Grevillea* hybrid 'Kay Williams', not patented, characterized by its light orange-colored inflorescences, medium green-colored foliage, and vigorous, upright growth habit. The new cultivar was discovered and selected as a single flowering plant within the progeny of the above stated cross-pollination during June 2009 in a controlled environment in in West Perth, Australia.

Asexual reproduction of the new cultivar by terminal stem cuttings since June 2009 in West Perth Australia and Valley Center, Calif. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Kings Celebration' as a new and distinct cultivar of *Grevillea* plant:

1. Bright red-colored inflorescences;
2. Medium green-colored foliage; and
3. Moderately vigorous, upright growth habit.

Plants of the new cultivar differ from plants of the female parent primarily in growth habit and from plants of the male parent primarily in inflorescence color.

Of the many commercially available *Grevillea* cultivars, the most similar in comparison to the new cultivar is 'Red Hooks', not patented. However, in side-by-side comparison, plants of the new cultivar differ from plants of 'Red Hooks' in at least the following characteristics:

1. Plants of the new cultivar have a leaf shape different from plants of 'Red Hooks';
2. Plants of the new cultivar have a bud color different from plants of 'Red Hooks'; and
3. Plants of the new cultivar have an inflorescence color that is a shade of red different from plants of 'Red Hooks'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Kings Celebration'. The plants were grown in two-gallon containers for approximately 19 months in a greenhouse in Valley Center, Calif.

Plants were then grown for two months outdoors in West Chicago, Ill. Plants were given one hard pinch approximately 8 to 10 weeks after transplant.

DETAILED BOTANICAL DESCRIPTION

Figure 1:
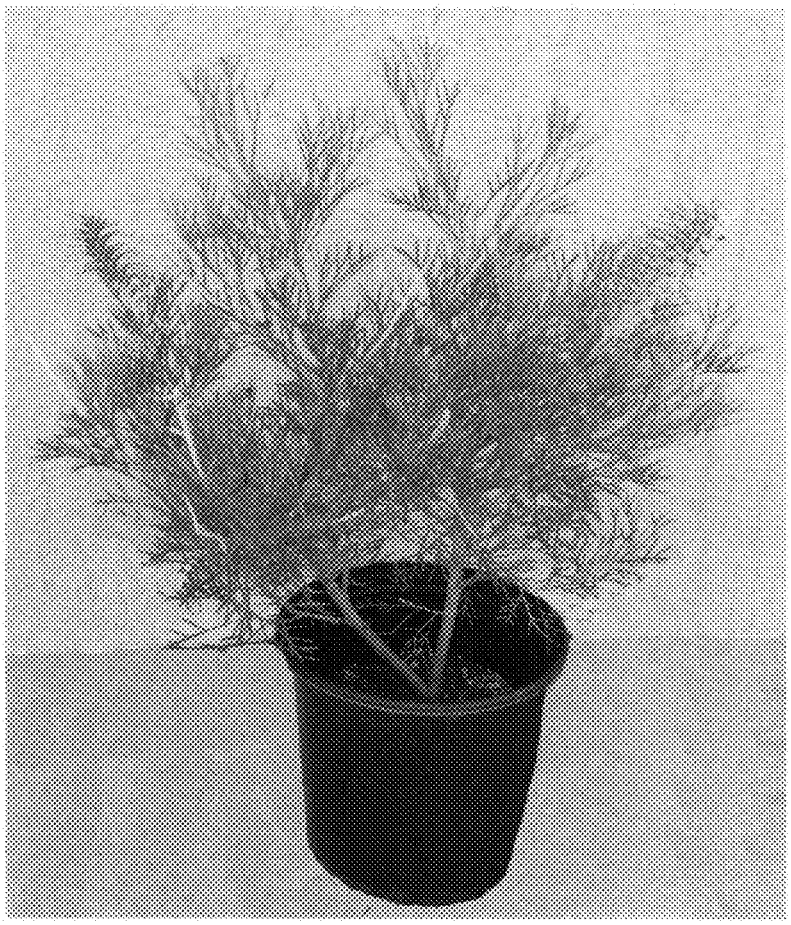
FIG. 1 illustrates a side view of the overall growth and flowering habit of 'Kings Celebration'.
Figure 2:
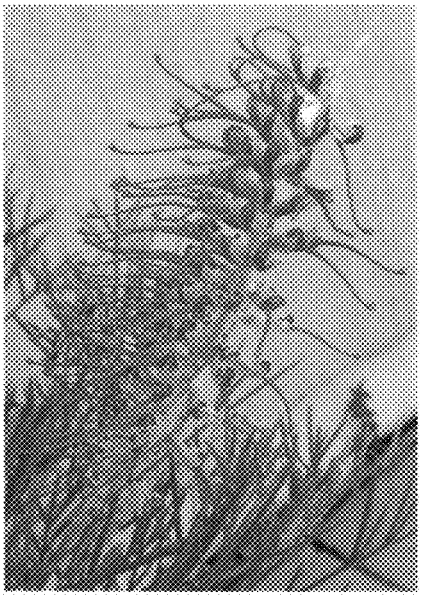
FIG. 2 illustrates a close-up view of the inflorescences of 'Kings Celebration'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in July 2015 under natural light conditions in West Chicago, Ill.

The following descriptions and measurements describe plants produced from cuttings from stock plants and grown in a poly-covered greenhouse without supplemental heating or cooling. Temperatures for this period ranged from an average high of 85° F. (29° C.) to an average low of 52° F. (11° C.). The plants were grown in Valley Center, Calif. in two-gallon containers for approximately 19 months utilizing a soilless growth medium. Plants were then grown for two months outdoors in West Chicago, Ill. Measurements and numerical values represent averages of typical plants.

Botanical classification: *Grevillea* hybrid cultivar Kings Celebration.

Parentage:

*Female parent.*—*Grevillea fastigiata* proprietary breeding selection not coded, not patented.

*Male parent.*—*Grevillea* hybrid 'Kay Williams', not patented.

Propagation:

*Type cutting.*—Terminal stem.

*Time to initiate roots.*—Approximately 12 to 16 weeks.

*Time to produce a rooted cutting.*—Approximately 20 to 24 weeks.

*Root description.*—Light brown in color, fine.

*Rooting habit.*—Freely branching, tight groupings of small rootlets.

Plant description:

*Commercial crop time.*—Approximately 16 to 24 weeks from a rooted cutting to finish in a one-gallon container.

*Growth habit and general appearance.*—Moderately vigorous, upright.

*Size.*—Height from soil level to top of plant plane: Approximately 52.0 cm. Width: Approximately 50 cm.

*Branching habit.*—Freely branching, pinching enhances branching. Quantity of main branches per plant: Approximately 2 trunks each with 6 branches.

*Branch.*—Strength: Strong. Length to base of peduncle: Approximately 17.0 cm. Diameter: Approximately 4.0 mm. Length of central internode: Approximately 2.0 cm. Texture: Tomentose. Color of young stems: N144A, color appears lighter due to pubescence. Color of mature stems: 199A with N200B.

Foliage description:

*General description.*—Form: Simple. Arrangement: Alternate. Fragrance: None detected.

*Leaves.*—Aspect: Acute angle to stem. Shape: 4 to 6 lobed, lobes linear and clustered near apex. Margin: Entire, pinnatisect; leaf margins curve downwards enclosing the lower surface of the leaf. Apex of lobes: Acute. Base: Narrowly attenuate. Venation pattern: Pinnate. Length of mature leaf: Approximately 9.0 cm. Width of mature leaf: Approximately 5.5 cm. Texture of upper surface: Immature leaves moderately pubescent, scattered silky hairs, becomes sparsely pubescent with development. Texture of lower surface: Tomentose with the exception of midvein. Pubescence color: NN155D. Color of upper surface of young foliage: 144A lobe tips tinted with N163B, color appears slightly lighter due to pubescence. Color of lower surface of young foliage: Closest to N144A, indistinguishable venation, color appears lighter due to pubescence. Color of upper surface of mature foliage: 137A with indistinguishable venation. Color of lower surface of mature foliage: 137D, indistinguishable venation, color appears slightly lighter due to pubescence.

Flowering description:

*Flowering habit.*—'Kings Celebration' is freely flowering under outdoor growing conditions with substantially continuous blooming in Zones 9a through 11.

*Lastingness of individual inflorescence on the plant.*—Approximately 3 weeks.

Inflorescence description:

*General description.*—Type: Raceme. Self-cleaning. Shape: Secund conflorescence, florets primarily facing one side. Aspect: Facing upward and outward. Arrangement: Terminal and from leaf axils. Fragrance: None detected. Quantity per plant: Approximately 3. Diameter: Approximately 7.0 cm. Depth: Approximately 10.5 cm.

*Bud.*—Rate of opening: Generally takes 4 to 6 days for bud to progress from first color to fully open floret.

*Bud just before opening.*—Shape: Globular. Diameter: Approximately 3.0 mm. Texture of outer surface: Tomentose. Pubescence color: NN155D. Color: 191B appears to be white due to pubescence.

*Florets.*—Quantity per inflorescence: Approximately 100. Arrangement: Primarily in pairs. Length: Approximately 2.7 cm. Diameter: Approximately 6.0 mm.

*Perianth.*—Shape: Tubular with a ventral limb, becomes revolute during anthesis. Length: Approximately 9.0 mm. Diameter at widest point: Approximately 6.0 mm. Diameter at base: Approximately 3.0 mm.

*Tepals.*—Quantity: 4. Shape: Linear. Margin: Entire. Apex: Acute. Length: Approximately 9.0 mm. Width: Approximately 2.0 mm. Texture of outer surface: Tomentose. Pubescence color: NN155D. Texture of inner surface: Glabrous. Color of outer surface when fully open: 61A, appears to be a lighter color due to pubescence. Color of inner surface when fully open: 61A to 61B.

*Peduncle*.—Strength: Strong. Aspect: Erect. Length: Approximately 1.5 cm. Diameter: Approximately 2.0 mm. Texture: Tomentose. Pubescence color: NN155D. Color: 145A, appears white due to pubescence.

*Rachis*.—Strength: Strong. Length: Approximately 10.5 cm. Diameter: Approximately 3.0 mm. Texture of outer surface: Tomentose. Pubescence color: NN155D. Color: 145A appears white due to pubescence.

*Pedicel*.—Strength: Strong. Aspect: Erect. Length: Approximately 1.0 mm. Diameter: Approximately 2.0 mm. Texture of outer surface: Tomentose. Pubescence color: NN155D. Color: 145D appears white due to pubescence.

*Reproductive organs*.—Androecium: Anthers located within perianth limb and basally attached to perianth. Anther quantity: 4 per floret. Anther shape: Bilobed. Anther length: Approximately 1.0 mm. Anther color: 163C with surface facing tepals of 200A. Pollen amount: Sparse. Pollen color: 163D. Gynoecium: Stigma functions as a pollen presenter holding pollen for pollinators to remove until stigma matures becoming receptive to cross pollination. Nectary located at base of ovary. Pistil quantity: 1 per floret. Pistil length: Approximately 2.7 cm. Stigma shape: Funnel. Stigma length: Less than 1 mm. Stigma color: 163A. Style length: Approximately 2.5 cm. Style color: 46A. Ovary length: Approximately 2.0 mm. Ovary texture: Tomentose. Pubescence color: NN155D. Ovary color: 145D, appears white due to pubescence. Nectary size: Approximately 1.0 mm in length and 2.0 mm in width. Nectary color: N163B with 163B at upper rim.

Seed and fruit production: Neither seed nor fruit production has been observed.

Disease and pest resistance: Resistance to pathogens and pests common to *Grevillea* has not been observed.

What is claimed is:

1. A new and distinct cultivar of *Grevillea* plant named 'Kings Celebration', substantially as herein illustrated and described.

* * * * *